(12) United States Patent
Tacon

(10) Patent No.: US 10,791,845 B2
(45) Date of Patent: Oct. 6, 2020

(54) THERAPEUTIC CUSHION

(71) Applicant: Gary Tacon, Piermont, NY (US)

(72) Inventor: Gary Tacon, Piermont, NY (US)

( * ) Notice: Subject to any disclaimer, the term of this patent is extended or adjusted under 35 U.S.C. 154(b) by 46 days.

(21) Appl. No.: 16/224,992

(22) Filed: Dec. 19, 2018

(65) Prior Publication Data
US 2019/0200774 A1 Jul. 4, 2019

Related U.S. Application Data

(60) Provisional application No. 62/612,783, filed on Jan. 2, 2018.

(51) Int. Cl.
*A47C 20/02* (2006.01)
*A47G 9/10* (2006.01)
*A61F 5/01* (2006.01)

(52) U.S. Cl.
CPC ............ *A47C 20/027* (2013.01); *A47G 9/109* (2013.01); *A47G 9/1081* (2013.01); *A47C 20/026* (2013.01); *A61F 5/01* (2013.01)

(58) Field of Classification Search
CPC ...... A47C 20/027; A47C 20/026; A47G 9/10; A47G 9/1072; A47G 9/1081; A47G 9/109; A61G 5/01
See application file for complete search history.

(56) References Cited

U.S. PATENT DOCUMENTS

| | | | | |
|---|---|---|---|---|
| 3,885,258 A | * | 5/1975 | Regan | A47C 27/144 5/727 |
| 4,494,261 A | * | 1/1985 | Morrow | A47G 9/109 5/636 |
| 4,665,573 A | * | 5/1987 | Fiore | A47C 27/148 5/731 |
| 5,279,310 A | * | 1/1994 | Hsien | A61F 5/01 128/DIG. 20 |
| 5,682,632 A | * | 11/1997 | Cotroneo | A47G 9/10 5/636 |
| 5,906,586 A | * | 5/1999 | Graham | A61F 5/04 128/845 |
| 5,987,675 A | * | 11/1999 | Kim | A47C 20/026 5/632 |
| 6,345,401 B1 | * | 2/2002 | Frydman | A47G 9/10 5/636 |
| 6,902,537 B1 | * | 6/2005 | Geisert | A61F 13/128 602/19 |
| 7,578,015 B1 | * | 8/2009 | Wilson | A47G 9/1036 5/636 |

(Continued)

*Primary Examiner* — Robert G Santos
*Assistant Examiner* — Rahib T Zaman
(74) *Attorney, Agent, or Firm* — Ladas & Parry LLP

(57) ABSTRACT

A therapeutic cushion comprising a one-piece, elongated, molded firm body, the forwardmost portions of said body in side elevation, including convexly contoured surfaces adapted for head-engaging support. Intermediate portions of said body in side elevation defining an upwardly projecting apex adapted for engaging support of the cervical vertebrae C-3 to C-6, the rearwardmost portions of said body in side elation being convexly contoured and downwardly shaped and adapted to support thoracic, lumbar, and sacral spinal regions, said body defining a concave gap in side elevation between said intermediate and said rearwardmost portions and whereby the geometry of said body gently stretches the spine of a user laying horizontally thereupon.

2 Claims, 4 Drawing Sheets

(56) References Cited

U.S. PATENT DOCUMENTS

| | | | | |
|---|---|---|---|---|
| 7,926,134 | B2* | 4/2011 | Carlos | A47G 9/10 |
| | | | | 5/640 |
| 9,089,230 | B2* | 7/2015 | Cho | A61F 5/01 |
| 9,801,480 | B1* | 10/2017 | McCain | A47C 7/383 |
| 9,808,370 | B1* | 11/2017 | Reser | A61F 5/56 |
| 10,350,452 | B2* | 7/2019 | McCarter | A63B 23/0205 |
| 2009/0100596 | A1* | 4/2009 | Weedling | A47C 20/027 |
| | | | | 5/81.1 HS |
| 2012/0037163 | A1* | 2/2012 | Jones | A47C 20/027 |
| | | | | 128/845 |
| 2012/0179202 | A1* | 7/2012 | Pham | A47G 9/1081 |
| | | | | 606/240 |
| 2012/0186025 | A1* | 7/2012 | Kardos | A47C 20/027 |
| | | | | 5/655.9 |
| 2013/0318722 | A1* | 12/2013 | Kim | A47G 9/1081 |
| | | | | 5/632 |
| 2014/0020184 | A1* | 1/2014 | Loth | A47G 9/109 |
| | | | | 5/640 |
| 2015/0040321 | A1* | 2/2015 | Moore | A47G 9/109 |
| | | | | 5/636 |
| 2015/0047646 | A1* | 2/2015 | Marinkovic | A47G 9/1081 |
| | | | | 128/845 |
| 2015/0351564 | A1* | 12/2015 | Vogel | A47G 9/1081 |
| | | | | 5/640 |
| 2016/0100701 | A1* | 4/2016 | McKnight | A47G 9/109 |
| | | | | 5/636 |
| 2016/0114708 | A1* | 4/2016 | Spalter | B60N 2/885 |
| | | | | 297/397 |
| 2017/0128307 | A1* | 5/2017 | Kim | A47G 9/109 |

* cited by examiner

THERAPEUTIC CUSHION

PRIORITY CLAIM

The application claims the benefit of U.S. Provisional Patent Application Ser. No. 62/612,783, filed Jan. 2, 2018.

BACKGROUND OF THE INVENTION

The present invention is a new and improved apparatus, a new therapeutic or so-called "Body Tuning Cushion™," for improving posture and gently flexing a user's spine into proper alignment with the head, arms, and shoulders.

Numerous spine-engaging devices are known to the art including those shown in U.S. Pat. Nos. 4,230,099; 5,180,386; 5,632,050; 5,797,154; 5,279,310; 5,987,675; 6,006,380; and 8,434,492. The disclosures of these references are understood to represent the state of the art.

SUMMARY OF THE INVENTION

The therapeutic or so-called "Body Tuning Cushion™" of the present invention provides a new and improved tuning apparatus for reconditioning the musculoskeletal system of the upper body (toward overcoming the negative impact gravity has upon the human spine), and the lower body (toward modifying how it supports a properly tuned and posed upper body). The primary objective of using the new therapeutic cushion is to utilize the effect of gravity while reducing muscular tension throughout the human body.

Daily use of the new therapeutic cushion introduces a unique quality of well-being and health awareness. The new therapeutic cushion is ergonomically designed to enhance the specific awareness of and the beneficial effect of gravity on the spine. The new device eases the spine into an enhanced supported condition. The user simply relaxes onto the new therapeutic cushion for very short time intervals; this provides a gentle flexion and stretching of the entire spine/torso while cradling the head.

Typically, all three vertebral sections of the spine (cervical, thoracic, and lumbar) have become habituated to supporting this upper body weight by settling into an often irretrievably compressed condition, while sitting or standing (resulting in poor posture). The new therapeutic cushion targets these three sections simultaneously flexing them into improved posture under the influence of gravity.

Specifically, the invention relies upon gravity to work effectively by actually allowing gravity to draw the arms and shoulders down into a corresponding alignment with the spine as the spine is oriented by the geometry of the new therapeutic cushion into proper posture.

Initially, three to five minutes of resting by a user laying horizontally upon the therapeutic cushion is preferred and is effective. However, there is no limit on the resting duration on the cushion, nor a limit to the number of times per day a user may use the cushion.

For a better understanding of the present invention and an appreciation of its attendant advantages, reference should be made to the accompanying drawings and the following detailed description.

DETAILED DESCRIPTION OF THE INVENTION

Referring to FIGS. 1-5, the new therapeutic cushion includes a head-engaging portion 30, an upwardly projecting apex portion 31 for engaging the back and the neck between cervical vertebrae C-3 to C-6 (vertebrae C-1 to C-6 are specifically numbered in FIG. 5); a "valley" 32 between the apex 31 and lower spine-engaging (thoracic, lumbar, sacral) portion 33. The new therapeutic cushion is fabricated from a medium density foam of the type well known in the cushioning art. An exemplary material for the therapeutic cushion body is polyurethane foam having the following properties:

| | |
|---|---|
| Density | 1.90 to 2.00 |
| IFD 25% | 50 to 60 |
| IFD 65% | 105 to 126 |
| Tensile PSI | 14 |
| Elongation % | 113 |
| Tear PLI | 1.11 |
| CS 90% | 3.5 |
| HACS % | 4.5 |
| Fatigue Loss % | 37.7 |
| *CAL 117-2013 | *Pass |

Physical testing was done in accordance with ASTM D 3574-05.
*This certifies that this foam passes CAL 117-2013.

The illustrated dimensions are exemplary for average sized individuals; it should be understood that these dimensions may be scaled upwardly or downwardly to accommodate much larger or smaller users.

Figure 1:
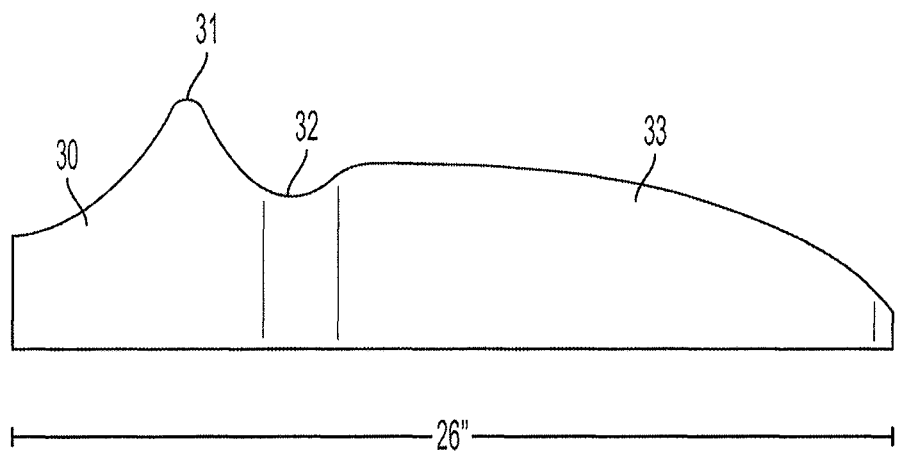
FIG. 1 is a side elevational view, with dimensions, of an exemplary therapeutic cushion embodying the principles of the invention.
Figure 2:
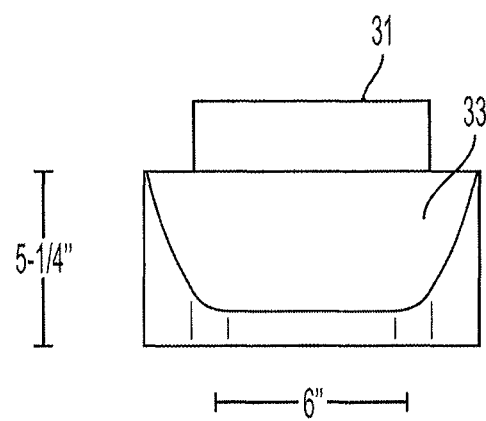
FIG. 2 is a first end view of the new therapeutic cushion of FIG. 1.
Figure 3:
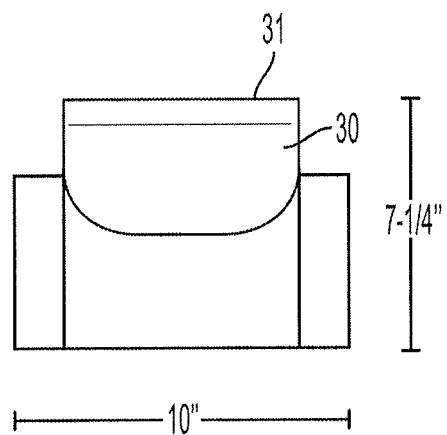
FIG. 3 is an opposite end view of the new therapeutic cushion.
Figure 4:
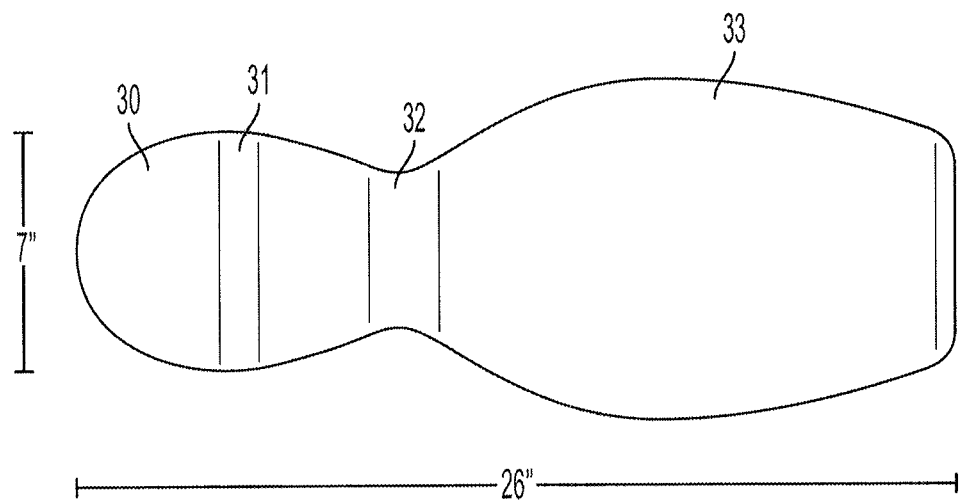
FIG. 4 is a to plan view of the new therapeutic cushion of FIG. 1.
Figure 5:
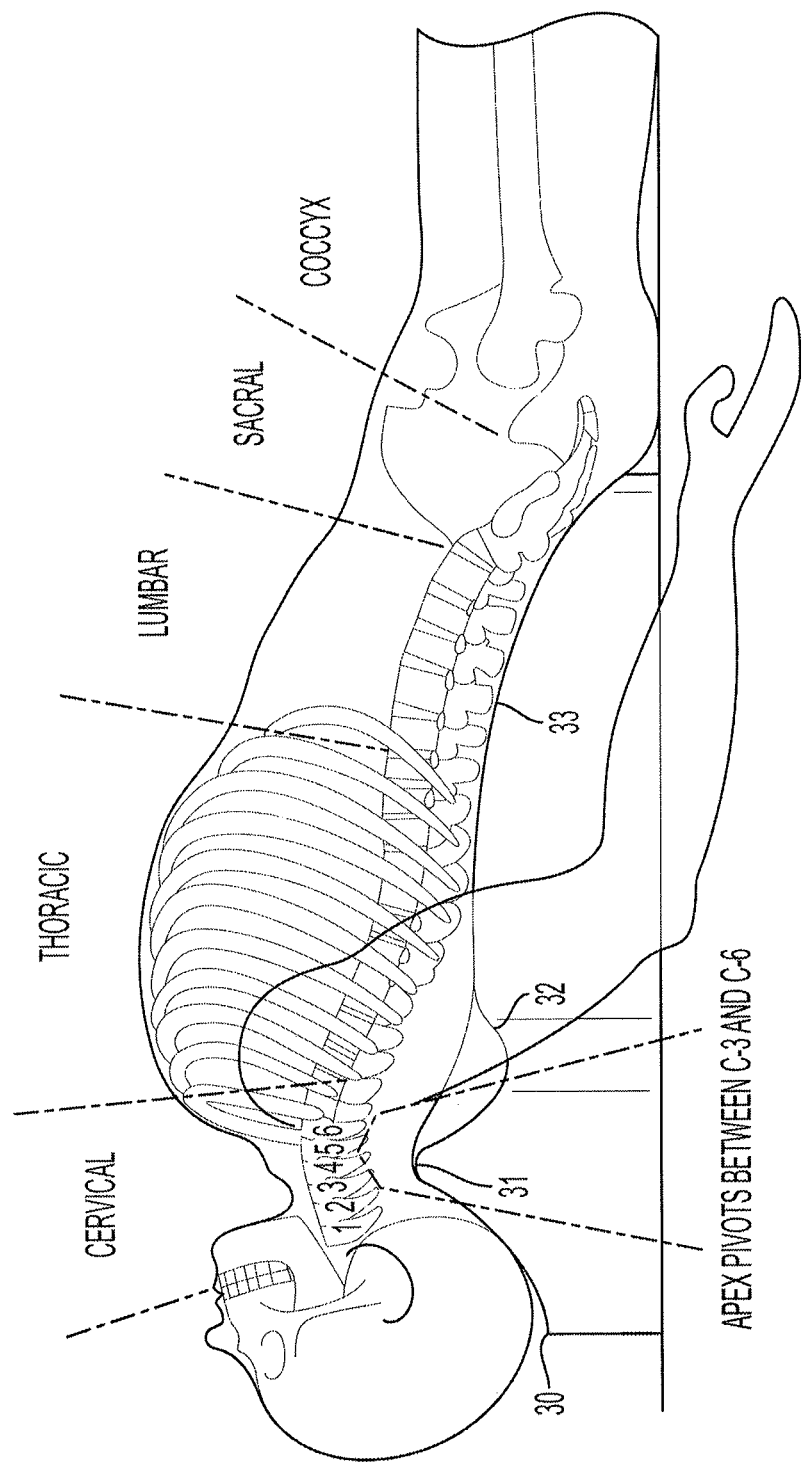
FIG. 5 is a side view of the new therapeutic cushion with a skeletal cross-section illustrating the engagement of the vertebrae with the upper surface.
Figure 8:
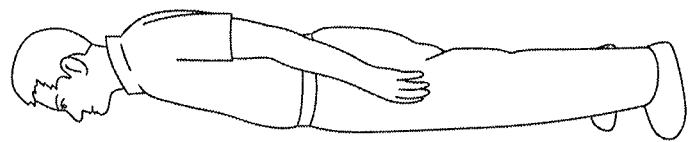
FIG. 8 is a side view of the user of FIGS. 6 and 7 after lying on the new therapeutic cushion for a short period of time.
Figure 7:
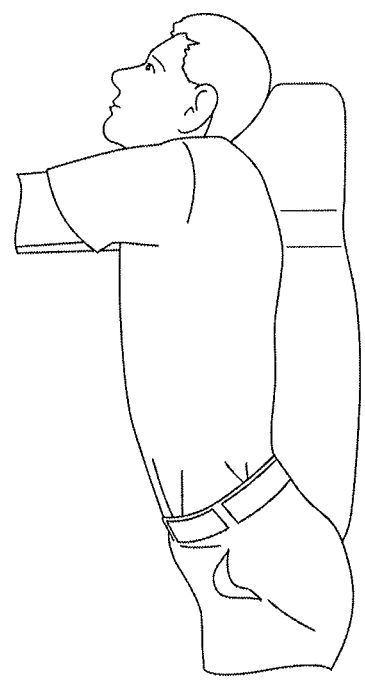
FIG. 7 is a view of a user lying down with his back fully engaged with the new therapeutic cushion.
Figure 6:
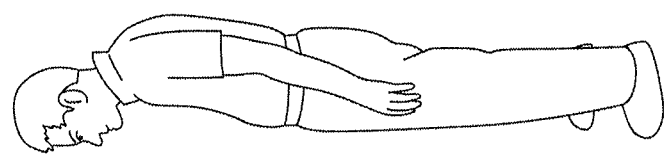
FIG. 6 is a side view of a prospective user before lying down on the new therapeutic cushion.

In use, the user simply relaxes onto the new therapeutic cushion as shown in FIGS. 5 and 7 for very short time intervals, which provide a gentle flexion to the entire spine while cradling the head. This flexion allows the spine to gradually realign by curving in the opposite direction to the effects of gravity. The user is instantly exposed to existing postural deficits, while being simultaneously led to a path of recreating the physical stature of the body in a new, simple, and easily sustainable way.

The new and improved therapeutic cushion provides temporary supported flexion or stretch of the seven cervical vertebrae, the twelve thoracic vertebrae, and the five lumbar vertebrae. Depending on the length of the user's spine, a portion of the sacrum (five fused lower vertebrae) may also be supported. The remaining lowest vertebrae section, the coccyx, is typically not supported by the cushion.

The new therapeutic cushion is molded or formed as a unitary dense foam shape having two distinct sections: the head cradle section and the torso support section. If desired, the unitary foam shape may be enveloped with a form-fitting cover fabricated from a soft, light-weight, washable fabric (not illustrated) or overcoated with a protective film (not illustrated).

The apex 31 of the head cradle section serves as a self-informing pivot point for the back of the neck at the base of the skull. This, in turn, dictates the manner in which the lower two main sections of the spine (thoracic and lumbar) will conform to the cushion as the user lays down upon it horizontally. Designed to be contour-fitted for the three upper sections of the spine, the apex initiates proper placement by gently receiving and supporting all seven cervical vertebrae, typically pivoting between C-3 and C-6. This permits the cervical spine to relax completely while initiating proper alignment for the lower sections of the spine.

While the head is supported so as to descend away from the neck and relax into the cradle, the torso is simultaneously supported so as to settle in the opposite direction away from the head and neck. This allows the spine to experience an impulse of a two directional passive traction, soothing the spine into a deeper relaxation than when merely lying flat and unsupported.

All twelve thoracic vertebrae and all five lumbar vertebrae experience a general quality of similarly supported flexion from the gently curved torso section 33 of the cushion. While potential users have different overall spinal lengths as well as differently sized vertebrae, the fundamental support region of this section typically ranges from the $6^{th}$ to the $10^{th}$ thoracic vertebrae, while the lumbar vertebrae benefit from being generally supported along their entire length.

It should be understood, of course, that the specific form of the invention herein illustrated and described is intended to be representative only, as certain changes may be made therein without departing from the clear teachings of the disclosure.

I claim:

1. A therapeutic cushion comprising:
   (a) a one-piece elongated, molded firm body fabricated from a polyurethane foam;
   (b) said polyurethane foam has the following properties as measured by ASTM D3574-05: Density=1.90 to 2.00 lbs. per cubic feet; IFD 25%=50 to 60; IFD 65%=105 to 126; Tensile PSI=1; Elongation %=113; Tear PLI=1.11; CS 90%=3.5; HACS %=4.5; Fatigue Loss % 37.7; said foam passes CAL 117-2013;
   (c) forwardmost portions of said body as viewed in side elevation, including convexly contoured surfaces adapted for head-engaging support;
   (d) intermediate portions of said body as viewed in side elevation, defining an upwardly projecting apex adapted for engaging support of the cervical vertebrae C-3 to C-6;
   (e) rearwardmost portions of said body as viewed in side elevation being convexly contoured and downwardly shaped and adapted to support thoracic, lumbar, and sacral spinal regions;
   (f) said body defining a concave gap, as viewed in side elevation, between said intermediate and said rearwardmost portions; and
   (g) whereby the geometry of said body gently stretches the spine of a user laying horizontally thereupon.

2. A therapeutic cushion fabricated from a dense polyurethane foam, said therapeutic cushion including
   (a) an elongated body portion having a flat base and a contoured upper surface adapted to engage a human body along spaced regions thereof;
   (b) said upper surface defining a head-engaging cavity at a forwardmost portion;
   (c) said upper surface defining an apex projecting upwardly therefrom and adapted to engage and support cervical portions of the spine of a user between vertebrae C-3 to C-6;
   (d) rearwardmost portions of said upper surface adapted to engage and support the 6th to 10th thoracic vertebrae;
   (e) said upper surface defining a concave portion between said rearwardmost and intermediate portions;
   (f) said polyurethane foam has the following properties as measured by ASTM D3574-05: Density=1.90 to 2.00 lbs. per cubic feet; IFD 25%=50 to 60; IFD 65%=105 to 126; Tensile PSI=1; Elongation %=113; Tear PLI=1.11; CS 90%=3.5; HACS %=4.5; Fatigue Loss % 37.7; said foam passes CAL 117-2013; and
   (g) whereby the upper surfaces cause flexion of the spine of a user laying horizontally thereupon when the user's spine engages and is supported thereby.

* * * * *